(12) United States Patent
Park et al.

(10) Patent No.: US 10,441,957 B2
(45) Date of Patent: Oct. 15, 2019

(54) MAGNETIC PARTICLE SEPARATING DEVICE, AND METHOD OF SEPARATING AND PURIFYING NUCLEIC ACID OR PROTEIN USING SAME

(71) Applicant: BIONEER CORPORATION, Daejeon (KR)

(72) Inventors: Han Oh Park, Daejeon (KR); Jong Kab Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 336 days.

(21) Appl. No.: 15/103,102

(22) PCT Filed: Dec. 5, 2014

(86) PCT No.: PCT/KR2014/011973
§ 371 (c)(1),
(2) Date: Jun. 9, 2016

(87) PCT Pub. No.: WO2015/088201
PCT Pub. Date: Jun. 18, 2015

(65) Prior Publication Data
US 2016/0368001 A1    Dec. 22, 2016

(30) Foreign Application Priority Data
Dec. 9, 2013    (KR) .................. 10-2013-0152613

(51) Int. Cl.
*B03C 1/01* (2006.01)
*C12N 15/10* (2006.01)
(Continued)

(52) U.S. Cl.
CPC ............... *B03C 1/288* (2013.01); *B03C 1/01* (2013.01); *B03C 1/0332* (2013.01);
(Continued)

(58) Field of Classification Search
CPC ... B03C 1/288; B03C 2201/18; B03C 1/0332; B03C 1/01; B03C 1/00; B03C 1/14; B01L 9/06; B01L 2400/043; G01N 33/54326
(Continued)

(56) References Cited

U.S. PATENT DOCUMENTS 4,895,650 A    1/1990   Wang
6,193,892 B1   2/2001   Krueger et al.
(Continued)

FOREIGN PATENT DOCUMENTS

EP          0136126 B1     6/1989
WO      WO 90-14891 A1    12/1990

OTHER PUBLICATIONS

European Search Report for EP Application No. 14 869 081.1 dated Aug. 7, 2017 from European Patent Office.
(Continued)

*Primary Examiner* — Claire A Norris
(74) *Attorney, Agent, or Firm* — Paratus Law Group, PLLC

(57) ABSTRACT

The present invention relates to a magnetic particle separating device, and a method of separating and purifying nucleic acid or protein using the same. The device comprises: induction magnets (100); an induction magnet fixing part (200) having induction magnet fixing holes (210) for fixing the induction magnets (100); and a body (300) in which entry holes (310) are formed into which tubes (T) are inserted. Thus, the application and removal of a magnetic field to and from the body is made very convenient, so that the device can be very advantageously used in the separation and purification of nucleic acid or protein.

8 Claims, 10 Drawing Sheets

(51) Int. Cl.
    *G01N 1/40* (2006.01)
    *B03C 1/28* (2006.01)
    *B03C 1/033* (2006.01)
(52) U.S. Cl.
    CPC ......... *C12N 15/1013* (2013.01); *G01N 1/405* (2013.01); *B03C 2201/18* (2013.01); *B03C 2201/26* (2013.01)
(58) Field of Classification Search
    USPC .................................................. 210/222, 695
    See application file for complete search history.

(56) References Cited

U.S. PATENT DOCUMENTS

| 6,409,925 | B1 | 6/2002 | Gombinsky et al. | |
|---|---|---|---|---|
| 2009/0028758 | A1 | 1/2009 | Su et al. | |
| 2009/0028759 | A1 | 1/2009 | Su et al. | |
| 2010/0225920 | A1 | 9/2010 | Xia et al. | |
| 2011/0088491 | A1 | 4/2011 | Krueger et al. | |
| 2011/0177592 | A1* | 7/2011 | Faustman | B03C 1/288 435/325 |
| 2011/0203997 | A1 | 8/2011 | Meyer | |
| 2012/0061302 | A1* | 3/2012 | Siddiqi | B01F 13/0809 210/138 |
| 2013/0026104 | A1 | 1/2013 | El-Fahmawi | |
| 2013/0260667 | A1* | 10/2013 | Agri, Sr. | F24F 13/082 454/254 |

OTHER PUBLICATIONS

Jan Svoboda, "6.5 Magnetic carriers and magnetic separation in biosciences", Magnetic Techniques for the Treatment of Materials, May 19, 2004, pp. 525-534.
International Search Report for PCT/KR2014/011973 dated Mar. 19, 2015 from Korean Intellectual Property Office.
Japanese Office Action for related JP application No. 2016-538731 dated Feb. 16, 2018 from Japanese Patent Office.

* cited by examiner

M: Bioneer 1kb ladder
1: Column type plasmid prep kit
2: Maglisto 2ml stand
3: Maglisto 15ml stand
4: Maglisto 50ml stand

MAGNETIC PARTICLE SEPARATING DEVICE, AND METHOD OF SEPARATING AND PURIFYING NUCLEIC ACID OR PROTEIN USING SAME

CROSS REFERENCE TO PRIOR APPLICATIONS

This application is a National Stage Patent Application of PCT International Patent Application No. PCT/KR2014/011973 filed on Dec. 5, 2014, under 35 U.S.C. § 371, which claims priority to Korean Patent Application No. 10-2013-0152613 filed on Dec. 9, 2013, which are all hereby incorporated by reference in their entirety.

TECHNICAL FIELD

The present invention relates to a magnetic particle separating device and a method of separating and purifying nucleic acid or protein using the same.

BACKGROUND ART

Separating nucleic acid (DNA or RNA) or protein from biological sample is most important process in a biological research and a diagnosis process. When nucleic acid is not separated from a sample, next processes such as gene detection, gene cloning, gene sequencing, gene amplification, cDNA synthesis, etc. cannot be performed. In order to separate DNA or RNA from various cell compound, effective and reproducible separating method is required, and a separating method using magnetic particles has been developed recently. According to the separating method using magnetic particles, a gene material is attracted to combine with magnetic particle and external magnetic field is applied to the test specimen to separate the gene material. In general, it is known that magnetic particles with size in a range of 500~2000 nm are proper for separating DNA, RNA, protein, etc.

U.S. laid open application number 2013/0026104 (MAGNETIC SEPARATION DEVICE AND METHODS) discloses a magnetic particle separating device for separating gene material through applying magnetic field.

Referring to specification and FIG. 3 of above patent application, the central support member 119 with magnetic elements 123 is installed roughly between the supporting structure 111 and the main support portion 201. On the other hand, the container 501 containing magnetic material together with gene material is installed at the main support portion 201 and the supporting structure 111.

According to the above patent application, a screw combination is required for the container 501 being combined with the magnetic separation device 101, which induces discomfort. Further, in order to remove magnetic fields, the container 501 should be separated again from the magnetic separation device 101, so that there exists much discomfort.

DISCLOSURE

Technical Problem

The technical problem of the present invention is to solve the conventional problems, and for easily applying or removing magnetic fields to the container (hereinafter, referred to as 'tube') to separate and to purify requested nucleic acid or protein from test specimen more quickly and more conveniently.

Additionally, the present invention is for that the tube containing test specimen is stably fixed to the device according to the invention to improve structural stability.

Technical Solution

The present invention comprises a plurality of induction magnets (100) with magnetic fields for attracting magnetic particles; an induction magnet fixing part (200) having induction magnet fixing holes (210) into which the induction magnets (100) are insulted for fixing the induction magnets (100); and a body (300) with which the induction magnet fixing part (200) is combined, the body (300) having entry holes (310) along a height direction such that the entry holes (310) correspond to array position of the induction magnets (100), and the body (300) having a compartment wall (320) for comparting one (310a) of the entry holes (310) and an adjacent entry hole (310b).

The compartment wall (320) of the present invention may comprise an insertion hole (321) formed along a longitudinal direction of the compartment wall (320), and a tube-fixing member (322) inserted into the insertion hole (321) and compressing outer surface of a tube (T) to be inserted into the entry hole (310) to fix the tube T to the body (300).

The body (300) of the present invention may comprise a groove portion (360) penetrating the compartment wall (320) along a longitudinal direction of the compartment wall (320) and formed at inside wall (312) for forming the entry hole (310); and a tube-fixing member (322) inserted into the groove portion (360) and compressing outer surface of a tube (T) to be inserted into the entry hole (310) to fix the tube T to the body (300).

A depth (D) of the entry hole (310) may be greater than a length (L) of the tube (T) such that a bottom surface (BS) of the tube (T) is spaced apart from a bottom surface (311) of the entry hole (310) by a distance (t) when the tube (T) is inserted into the entry hole (310).

An end portion (211) of the induction magnet fixing holes (210) may protrude for fixing the induction magnet (100) when the induction magnet is inserted into the induction magnet fixing holes (210).

The induction magnet fixing part (200) may have a first combination magnet fixing hole (220) formed at edge portion of a surface on which the induction magnet fixing holes (210) are formed, the first combination magnet fixing hole (220) receiving a first combination magnet (230) for a combination with the body (300), and the body (300) may have a second combination fixing hole (330) formed at position corresponding to the first combination magnet fixing hole (220), the second combination fixing hole (330) receiving a second combination magnet (340) for a combination with the induction magnet fixing part (200) through a magnetic force.

A first end of the induction magnets (100) may be fixed to the induction magnet fixing holes (210) of the induction magnet fixing part (200), and a second end opposite to the first end may protrude upward. And the entry hole (310) may have an upper portion and a lower portion smaller than the upper portion in a cross-sectional area, for providing a lower portion of the body (300) with a space for the induction magnets (100) to be disposed between the compartment wall (320) and an adjacent compartment wall (320a).

The present invention may further comprise a body position fixing part (400) disposed between the body (300) and the induction magnet fixing part (200), the body position fixing part (400) comprising: a compressing member (410) for compressing an outer surface of the body (300) for the body (300) to be fixed to the induction magnet fixing part (200) to which the induction magnets (100) are fixed; and a receiving portion (420) receiving and fixing the compression member (410).

A method of separating and purifying nucleic acid or protein using the magnet particle separating device of the present invention, comprises mixing magnetic particles with gene material to provide a mixture to the tube (T) in order to separate nucleic acid by using magnetic particles (S100); fixing the tube to the body (300) (S200); combining the induction magnet fixing part (200) with the induction magnets (100) fixed thereto with the body (300) (S300); attracting magnetic particles combined with the gene material toward the induction magnets (100) through magnetic fields generated by the induction magnets (100) (S400); removing residue solution except for the magnetic particles combined with the gene material from the from the tube (T) (S500); and separating the induction magnet fixing part (200) from the body (300) to remove magnetic fields applied to the body (300) (S600).

The method may further comprise providing cleaning solution or separation solution to the tube (T) for separate the nucleic acid or protein from the magnetic particles in the tube (T) (S700) after removing magnetic fields (S600).

Advantageous Effects

According to the present invention, applying and removing magnetic fields are convenient. Therefore, it can be effectively used for extracting nucleic acid or protein.

Further, the tube can be easily inserted into and tightly fixed to the body so that residue material can be easily removed while the nucleic acid and the magnetic particles are attracted by magnetic material.

MODE FOR INVENTION

After additionally providing ethanol, distilled water or elution solution to particle assembly for separating protein, the present invention will be explained referring to FIGS.

Figure 4:
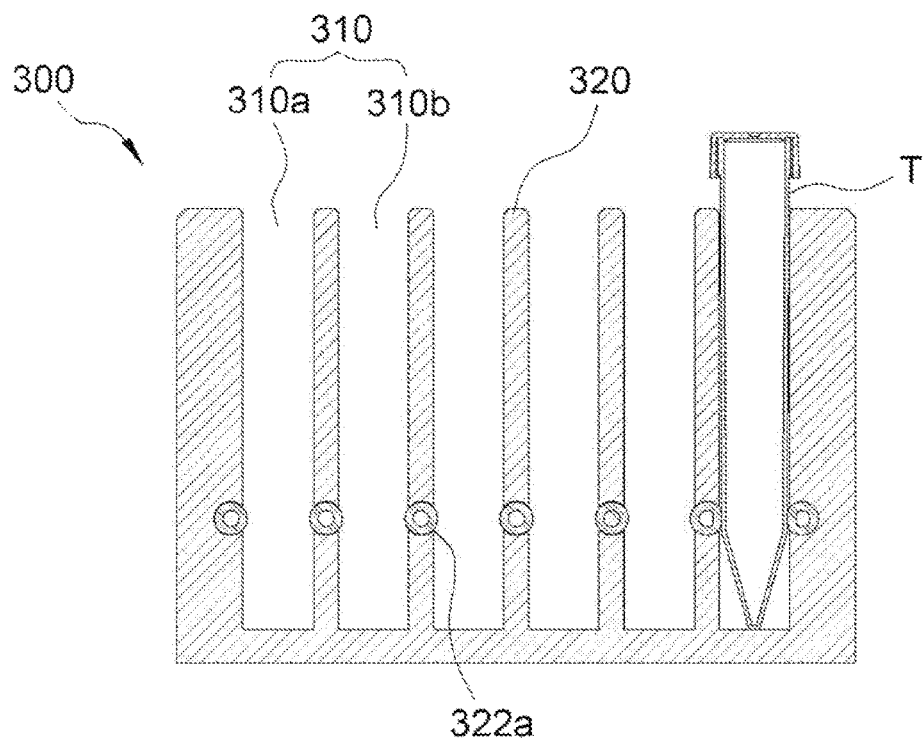
FIG. 4 is a side cross-sectional view of the magnetic particle separating device according to the embodiment.
Figure 5:
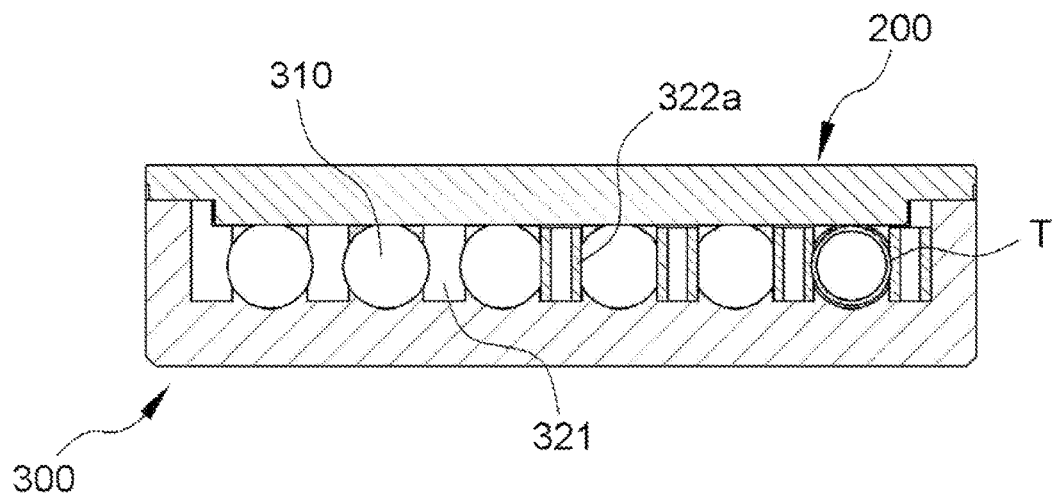
FIG. 5 is an upper face cross-sectional view of the magnetic particle separating device according to the embodiment.
Figure 6:
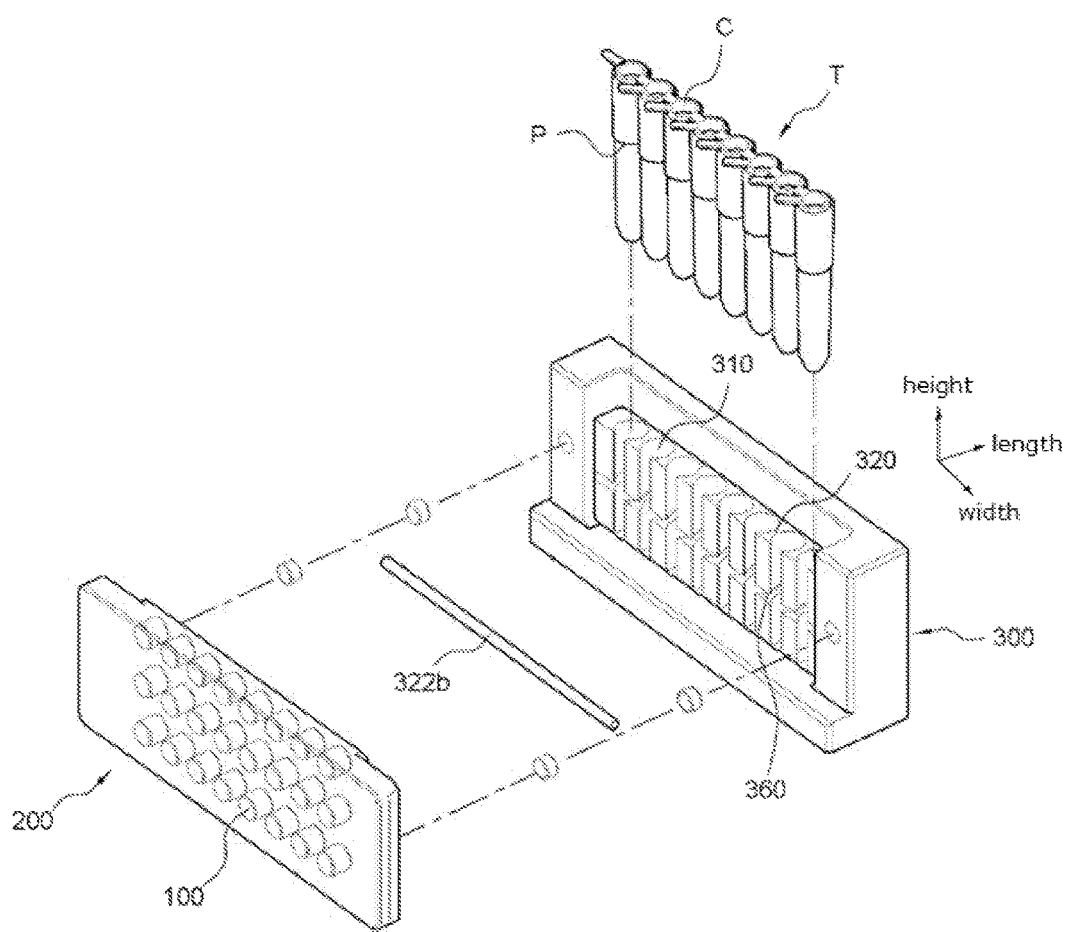
FIG. 6 is an exploded conceptual view showing the magnetic particle separating device according to another embodiment the present invention, viewing in one directional angle.
Figure 7:
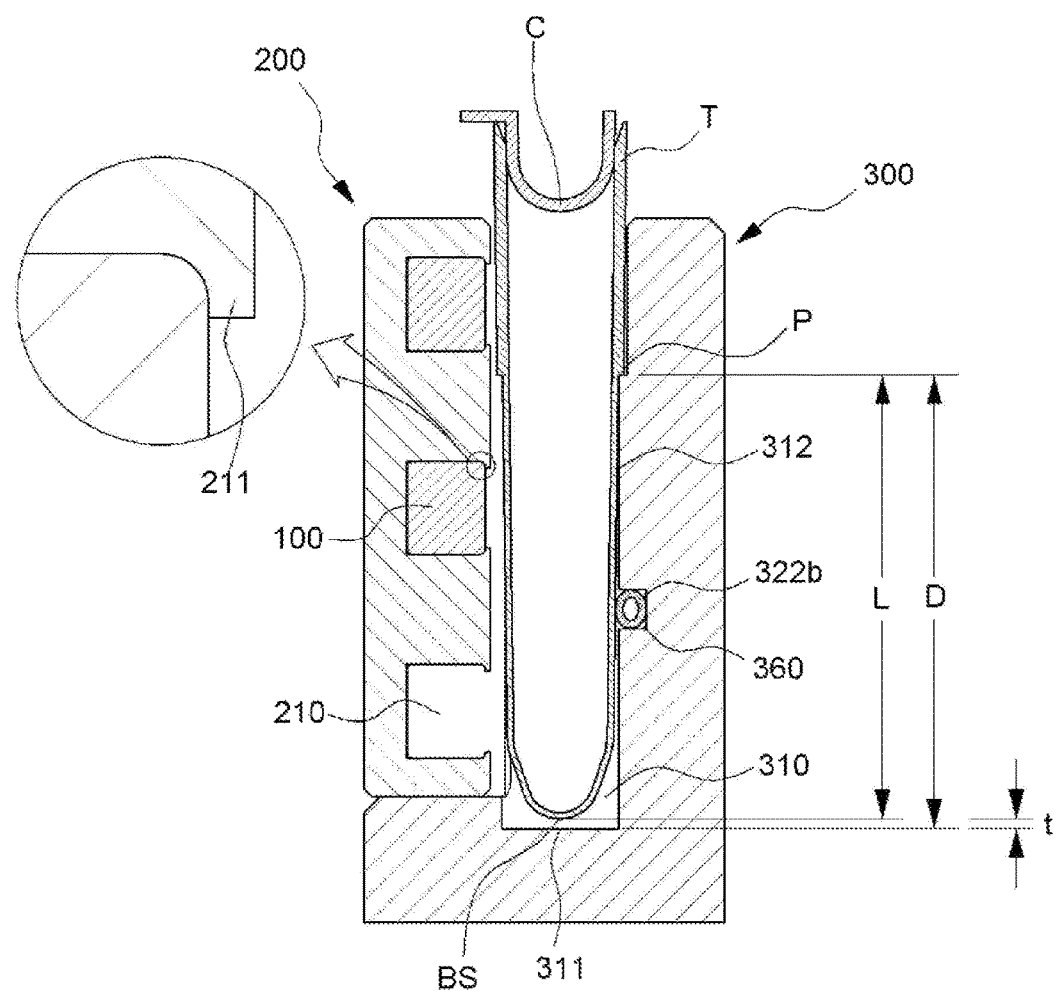
FIG. 7 is a side cross-sectional view of the magnetic particle separating device according to another embodiment.
Figure 8:
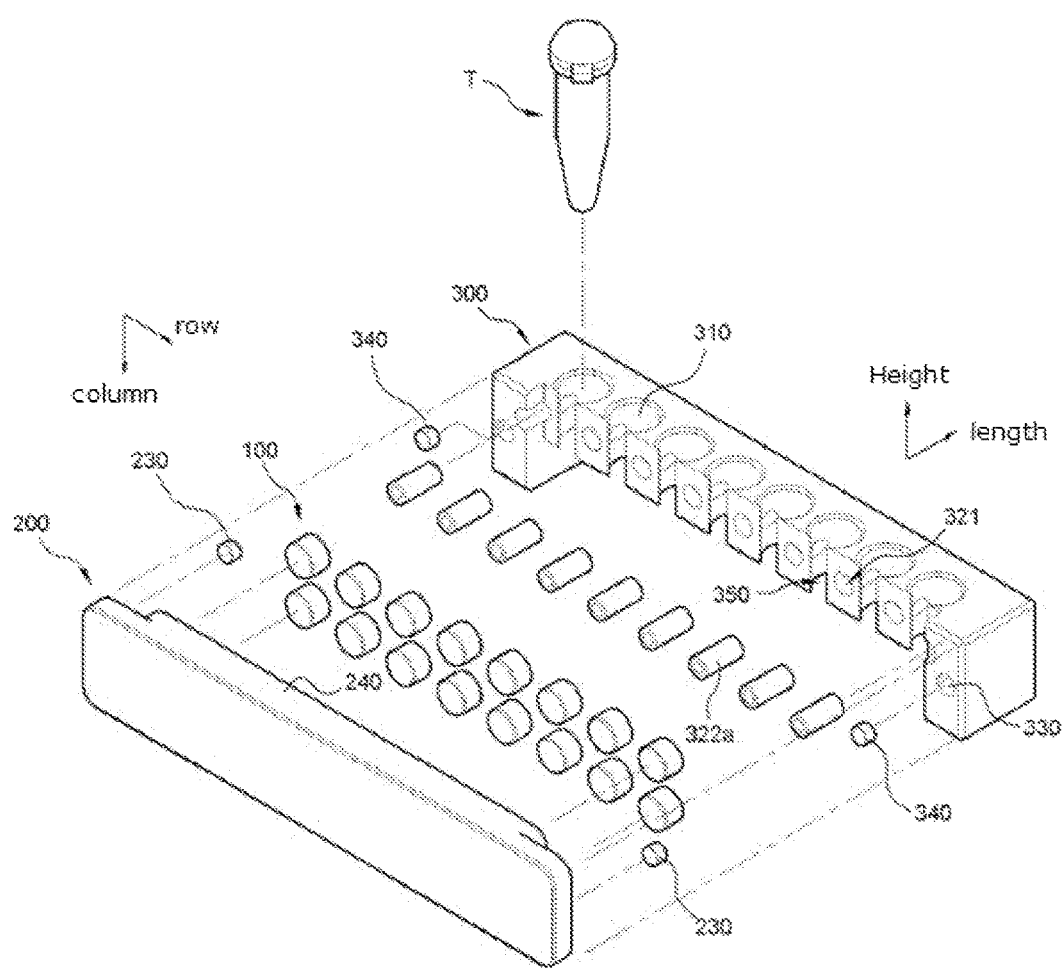
FIG. 8 is a side cross-sectional view of the magnetic particle separating device according to a third embodiment.
Figure 9:
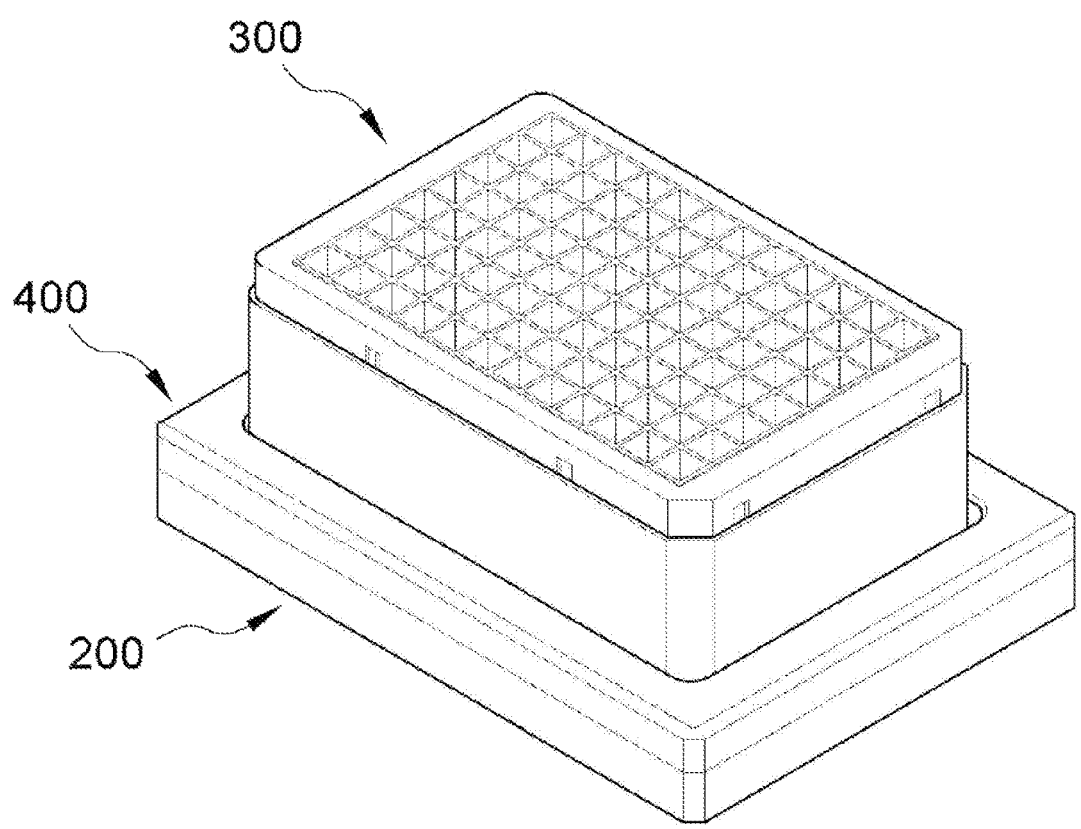
FIG. 9 is a conceptual view showing a magnetic particle separating device according to a fourth embodiment of the present invention.
Figure 10:
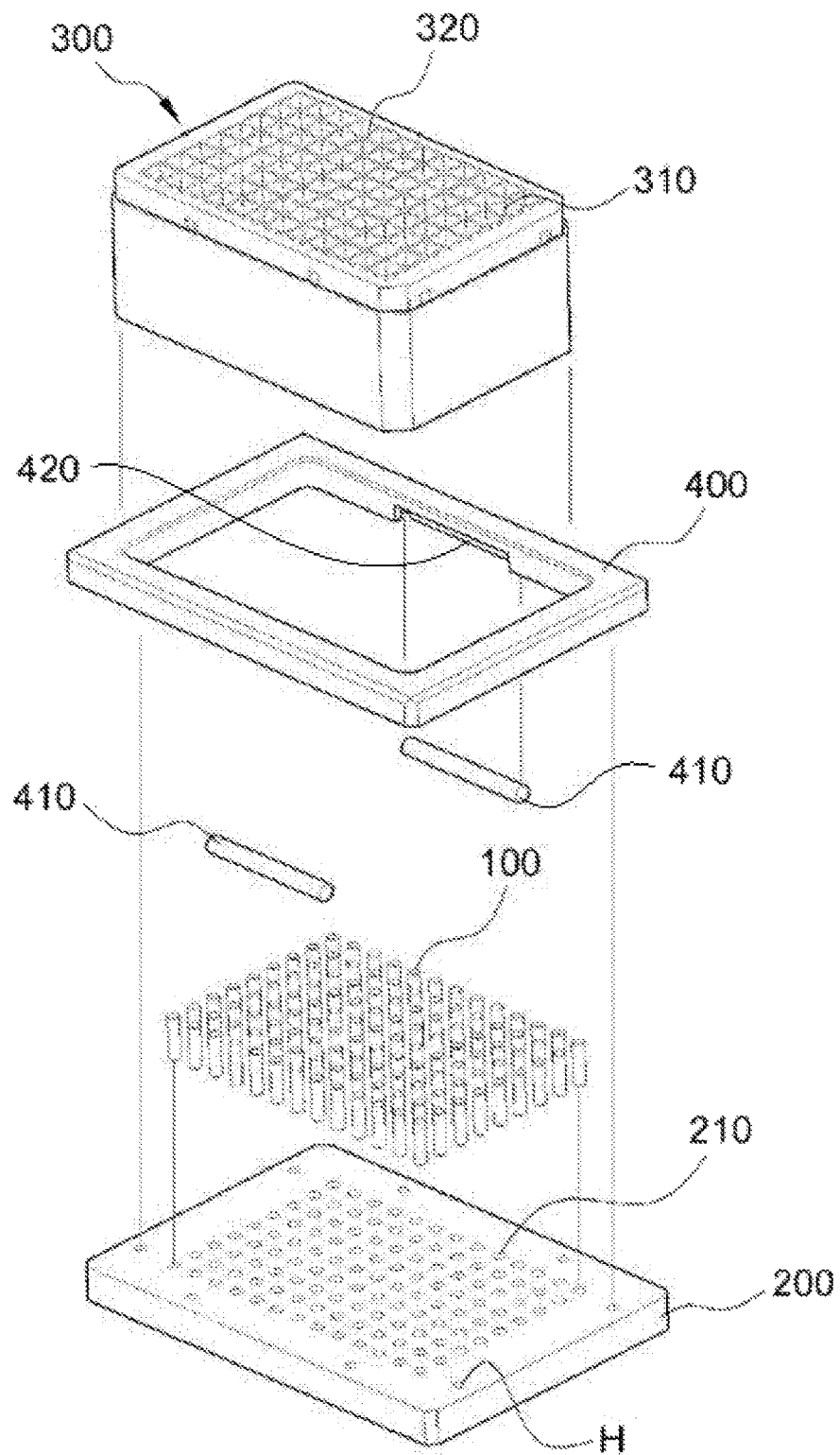
FIG. 10 is an exploded conceptual view showing the magnetic particle separating device according to the fourth embodiment.
Figure 11:
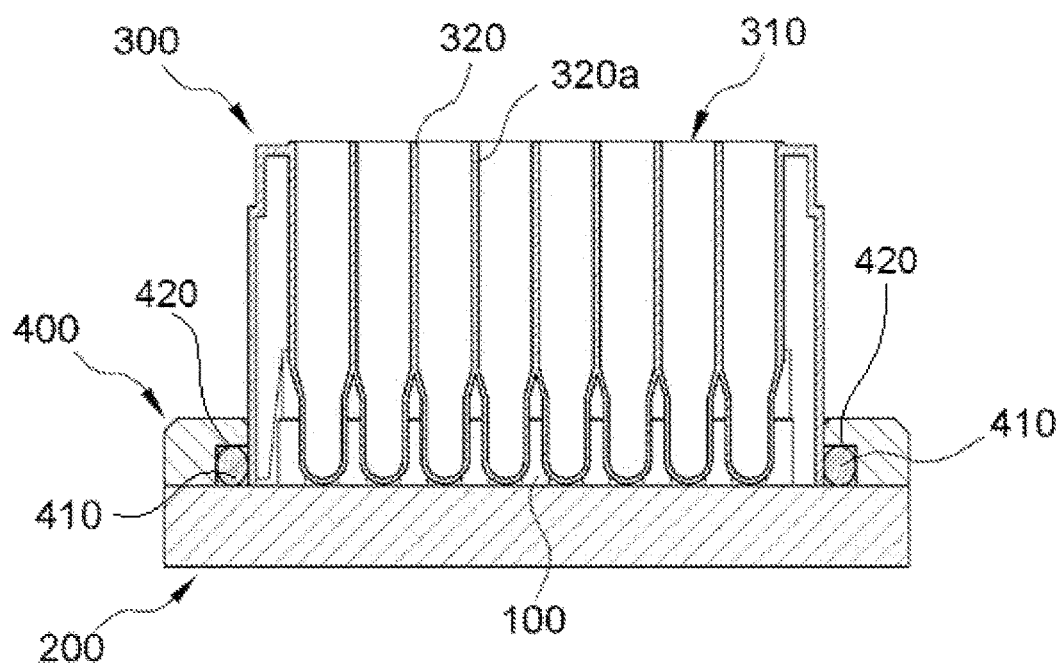
FIG. 11 is a side cross-sectional view of the magnetic particle separating device according to a fourth embodiment.

FIG. 1 through FIG. 5 correspond to a first embodiment of the present invention, FIG. 6 and FIG. 7 correspond to second embodiment of the present invention, FIG. 8 corresponds to a third embodiment of the present invention, and FIG. 9 through FIG. 11 correspond to a fourth embodiment of the present invention.

[First Embodiment] Tube Insertion Type Magnetic Particle Separating Device

At first, referring to FIG. 1 through FIG. 5, the first embodiment will be explained.

Figure 1:
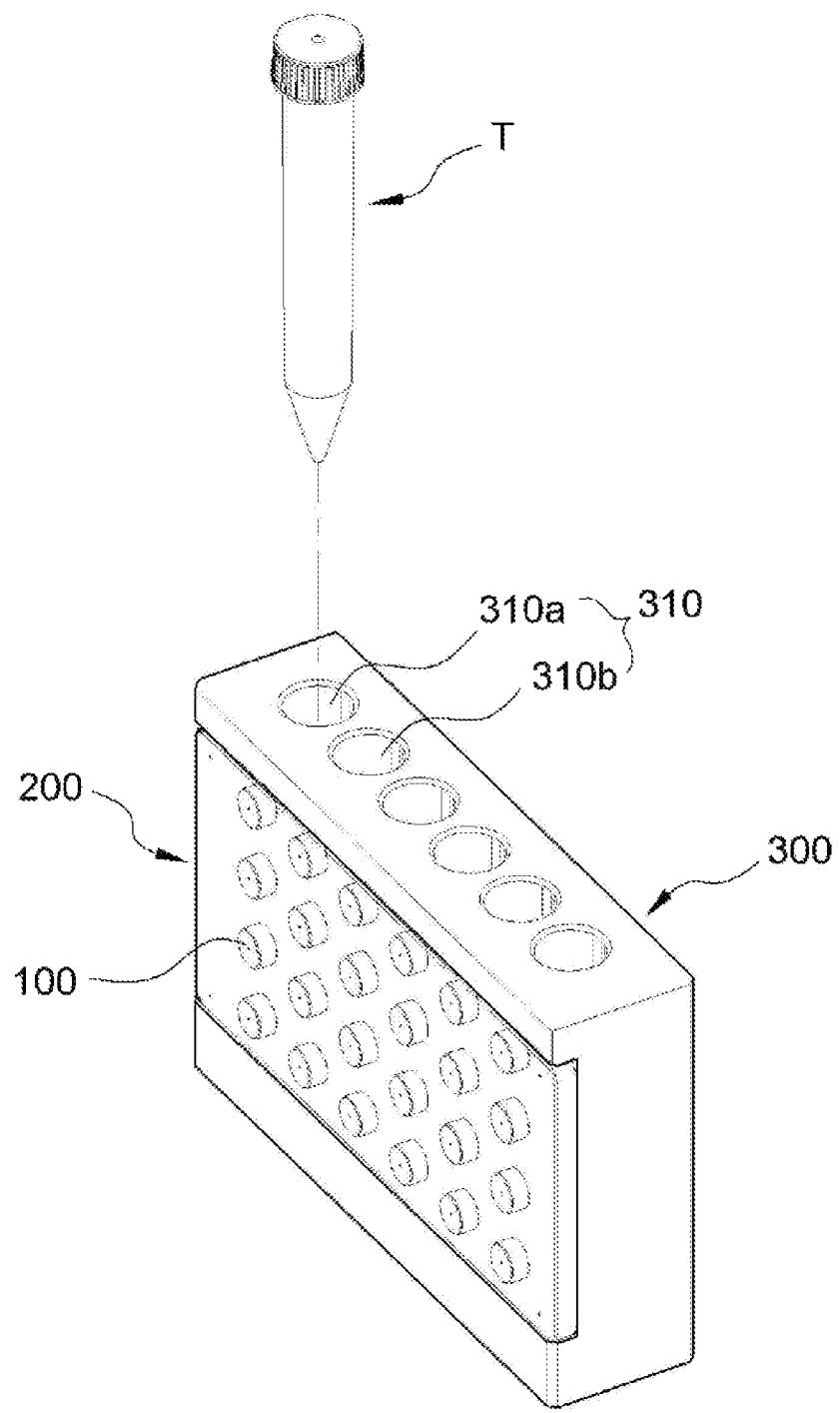
FIG. 1 is a conceptual view showing a magnetic particle separating device according to an embodiment of the present invention.

Referring to FIG. 1, according to the present invention, a body 300 having a plurality of entry holes 310 into which a tube (T) with a cylindrical shape can be inserted, and an induction magnet fixing part 200 at which an induction magnet 100 installed are equipped.

The induction magnet fixing part 200 has a plate shape, and is connected to a side of the body 300.

Figure 2:
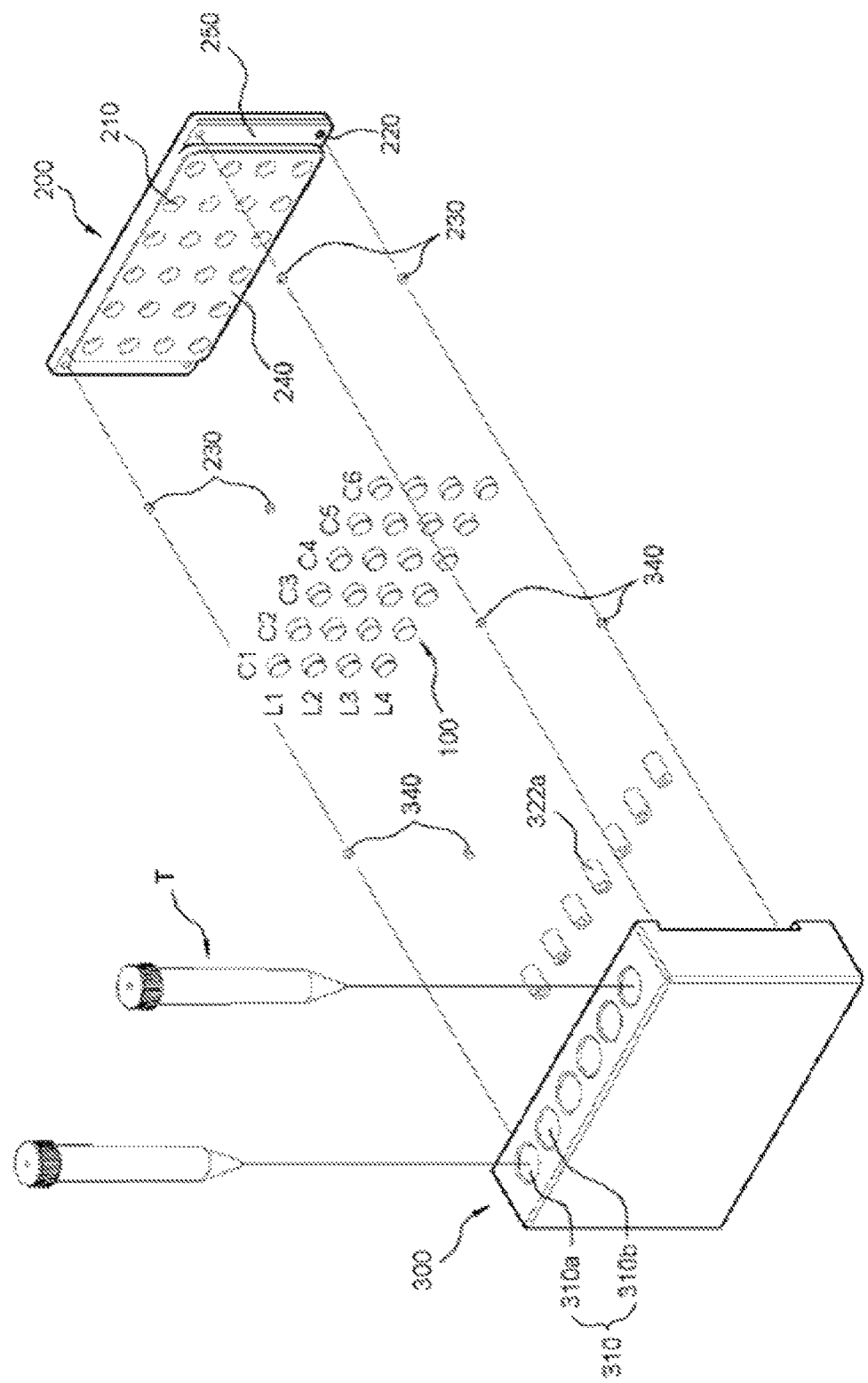
FIG. 2 is an exploded conceptual view showing the magnetic particle separating device according to the embodiment, viewing in one directional angle.

Referring to FIG. 2, the induction magnets 100 are material with magnetism, and has, preferably, magnetic force capable of inducing magnetic fields in the body 300 or the tube T inserted into the body 300 overall. In FIG. 2, the induction magnets 100 have a circular cross-sectional shape with some thickness as a coin. However, the induction magnets 100 may have various shapes, for example, a rectangular shape, a hexagonal shape, an octagonal shape, etc., as long as the induction magnets 100 are fixed to the induction magnet fixing holes 210 of the induction magnet fixing part 200.

Each of the induction magnets 100 is inserted into the induction magnet fixing holes 210 of the induction magnet fixing part 200 to be fixed. The induction magnets 100 are arranged along a plurality of rows L1, L2, L3, L4 and along a plurality of columns C1, C2, C3, C4, C5, C6. Preferably, one of the columns C1, C2, . . . , C6 is arranged such that the one corresponds to one tube T. Forming the plurality of rows L1, L2, . . . L4 is for effectively applying magnetic fields to the tube T. The rows and columns along which the magnets are arranged, may be variously change according to the size and the number of the tube T.

Referring to FIG. 2, the induction magnet fixing part 200 of the present invention has a plurality of induction magnet fixing holes 210, and a combination magnet fixing hole 220 and combination magnet 230 inserted into and fixed to the combination magnet fixing hole 220 for being combined with body 300 that is to be explained. Referring to FIG. 2, the number of columns of the induction magnet fixing holes 210 is six, so that it is preferable that the number of entry hole 310 of the tube T is six. That means that the number of columns can be changeable according to the number of entry holes 310. On the other hand, the number of entry holes 310 may be changeable according to the size and the number of tube T that is to be inserted.

Referring to FIG. 1 and FIG. 2, a face of the body 300, with which the induction magnet fixing part 200 is combined, may be dented, so that the body 300 and the induction magnet fixing part 200 may have a rectangular parallelepiped shape, when the body 300 and the induction magnet fixing part 200 are combined with each other. That is, the body 300 has a receiving portion (350, see FIG. 3) receiving the induction magnet fixing part 200. On the other hand, a first plate 240 of the induction magnet fixing part 200, at which the induction magnet fixing holes 210 are formed, may protrudes, with reference to a second plate 250 of the induction magnet fixing part 200, at which the combination magnet fixing hole 220. Hereinbefore, the first plate 240 and the second plate 250 of the induction magnet fixing part 200 are explained separately, but the first plate 240 and the second plate 250 may be integrally formed. By protruding of the first plate 240 with reference to the second plate 250, the first plate 240 gets closer to the entry hole 310 so that magnetic fields applied to the tube T can be strengthened.

Figure 3:
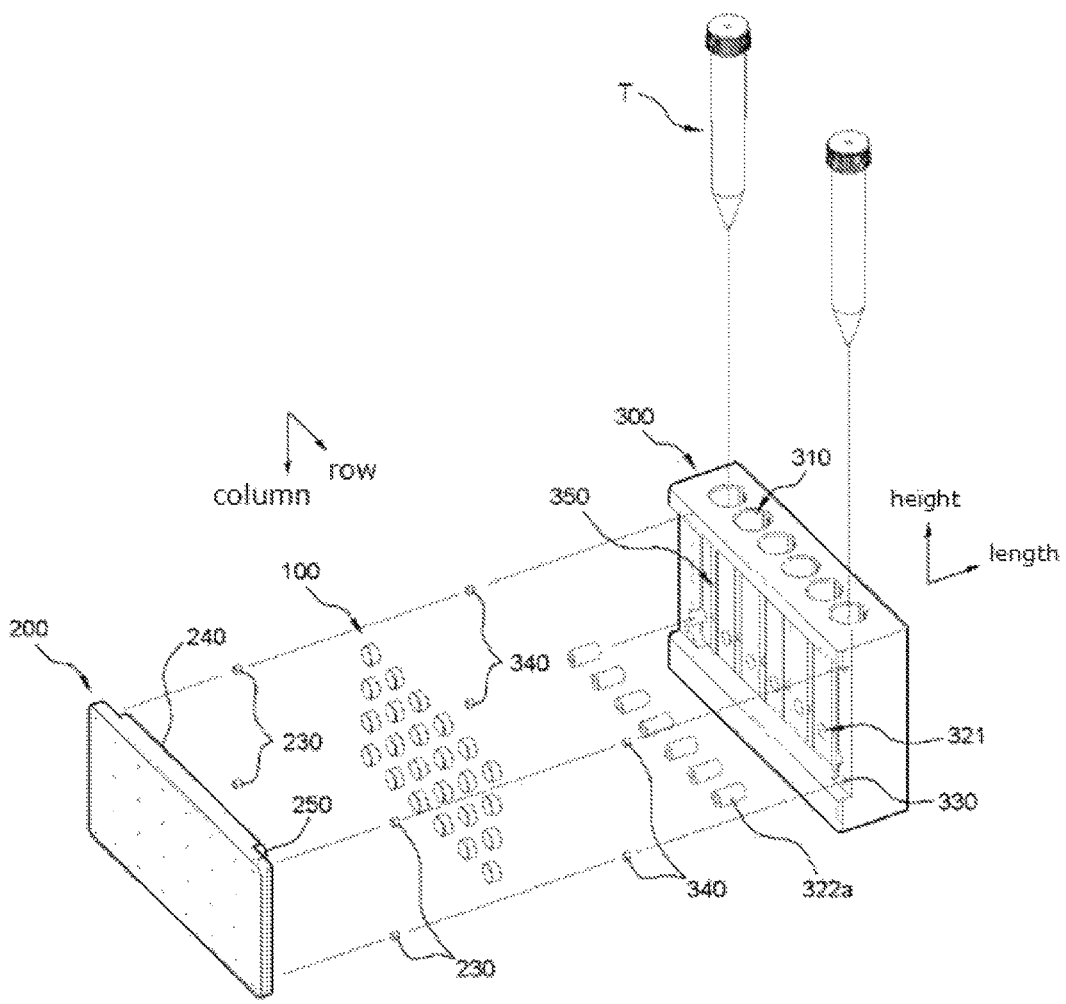
FIG. 3 is an exploded conceptual view showing the magnetic particle separating device according to the embodiment, viewing in another directional angle.

Referring to FIG. 2 through FIG. 4, the body 300 includes the entry holes 310 into which the tube T is inserted. In order to compart between a specific entry hole 310*a* and a neighboring entry hole 310*b*, a compartment wall 320 is formed. The compartment wall 320 has an insertion hole 321 penetrating along a lengthwise direction. A tube-fixing member 322*a*, of which outer surface protrudes toward inside of the entry hole 310, is inserted into the insertion hole 321.

Referring to FIG. 2 and FIG. 3, a first combination magnet fixing hole 220 formed at the corner of the induction magnet fixing part 200, and a first combination magnet 230 inserted into the first combination magnet fixing hole 220 are provided to the induction magnet fixing part 200. A second combination magnetic fixing hole 330 formed at corresponding position of them, and a second combination magnet 340 combined with the second combination magnetic fixing hole 330 are provided to the body 300. Through the magnetic force between the first combination magnet 230 of the induction magnet fixing part 200 and the second combination magnet 340 of the body 300, the induction magnet fixing part 200 and the body 300 can be combined with each other.

Referring to FIG. 2 and FIG. 3, the receiving portion 350 formed such that the first plate 240 and the second plate 250 of the induction magnet fixing part 200 are stably combined, is provided as explained above.

On the other hand, the body 300 can be made of transparent material, for example transparent acrylic so that separation of nucleic acid and magnetic material from the tube T can be conformed through naked eyes.

Referring to FIG. 4 and FIG. 5, tube-fixing member 322*a* is inserted into the compartment wall 320 to compress an outer surface of the tube T, when the tube T is inserted into the entry hole 310.

The insertion hole 321 is formed at each of the compartment wall 320 formed at the body 300. It is preferable that a side of the tube-fixing member 322*a* protrudes toward inside of the entry hole 310, when the tube-fixing member 322*a* is inserted into the insertion hole 321. Preferably, the tube-fixing member 322*a* is made of nonslip material such as rubber or silicone. Especially, a silicone o-ring with an internal hollow is preferable. Therefore, when the tube T is inserted, the tube-fixing member 322*a* does not excessively compress the tube T for preventing damage of the tube T.

Through the tube-fixing member 322*a* using the silicone o-ring, the tube T is compressed and fixed to the body 300, so that the tube T cannot easily separated from the body 300. When nucleic acid and magnetic material are separated in the tube T by magnetic fields of the induction magnets 100 fixed to the induction magnet fixing part 200, residue solution can be easily removed by flipping the body 300.

Further, according to the present invention, the first and/or the second combination magnets 230 and 340 are used for easy combination and separation of the induction magnet fixing part 200 and the body 300, so that magnetic fields of the induction magnet 100 can be easily applied to or removed from the body 300.

After cleaning solution, nucleic acid or protein separation solution, etc. are provided to the tube T to react them under the state that the induction magnet fixing part 200 is separated from the body 300, the induction magnet fixing part 200 is combined with the body 300 to apply magnetic fields. Then, the magnetic particles are attracted toward the induction magnetic fixing part 200 to be separated from supernatant. Therefore, the separated supernatant can be easily removed or collected to be recycled and nucleic acid or protein can be easily separated.

In the present embodiment, the magnetic particles manufactured by the invention of Korean Patent No. 10-10583023 or AccuBead™ manufactured by Bioneer corporation can be used as the magnetic particle used for the present invention, but not limited to them and other magnetic particles used for separating and purifying nucleic acid or protein by a person having ordinary skill in the art can be used.

[Second Embodiment] Another Tube Insertion Type Magnetic Particle Separating Device On the other hand, another tube insertion type magnetic particle separating device will be explained referring to FIG. 6 and FIG. 7.

The technical features common with the first embodiment will be omitted for effectiveness of description. Therefore, the technical features not described in the present embodiment are same as the previous embodiment.

Referring to FIG. 6 and FIG. 7, a side of the entry hole 310 is opened such that a cross-section thereof has a C-shape. A groove portion 360 is formed from a side of the compartment wall 320 to an inside wall 312 of the body 300 along a longitudinal direction of the body 300. A tube-fixing member 322*b* is inserted into the groove portion 360 with a line-shape along a wide-direction. The tube-fixing member 322*b* can be made of the same material as that of the first embodiment.

Referring to FIG. 6 and FIG. 7, as the tube-fixing member 322*b* is inserted into the groove portion 360, the tube-fixing member 322*b* compresses the outer surface of the tube T. In order to compress the outer surface of the tube T when the tube T is inserted, it is preferable that a diameter of the tube-fixing member 322*b* is greater than a length of the groove portion 360 formed at the inside wall 312. That is, a portion of the tube-fixing member 322*b* may protrude out of the entry hole 310.

Referring to FIG. 6 and FIG. 7, when the tube T is inserted into the entry hole 310, a bottom surface BS of the tube T and a bottom surface 311 of the entry hole 310 may be spaced apart by a specific distance t. That is the same in the first embodiment. That is for preventing damage of the tube T when the tube T is inserted and the magnetic particle separating device is used. In order for that, the height of the compartment wall 320 formed at the body 300 may be designed to be smaller than the height of the body 300. A stepped portion P may be formed at an upper portion of the compartment wall 320 to seize the tube T. That is, a stepped portion P of the tube T is seized by an upper portion of the compartment wall 320. Alternatively, the diameter of the tube T may gradually increase so that the tube T may be seized by the compartment wall 320.

Referring to FIG. 7, in order to fix the induction magnets 100 inserted into the induction magnet fixing part 200 effectively, an end portion 211 of the induction magnet fixing holes 210 may designed to protrude. In order for a tight fit of the induction magnet 100 when the induction magnet 100 is inserted into the induction magnet fixing hole 210, the end portion 211 protrudes. Due to the different size of the entry of the induction magnet fixing holes and the induction magnet 100, the induction magnet 100 is tightly and stably fixed to the induction magnet fixing hole 210.

Referring to FIG. 7, it is preferable that the upper end portion of the tube T is chamfered so that a cap C of the tube T can effectively plug up the tube T. That is for convenience of installation.

[Third Embodiment] Third Tube Insertion Type Magnetic Particle Separating Device On the other hand, still another tube insertion type magnetic particle separating device will be explained referring to FIG. 8.

The technical features common with the first and second embodiments will be omitted for effectiveness of description. Therefore, the technical features not described in the present embodiment are same as the previous embodiments.

Referring to FIG. 8, a lower portion of the body 300 may be opened. In order to prevent damage of the tube T when the tube T is inserted into the entry hole 310, it is preferable that the tube T does not reach to a bottom surface of a table. Alternatively, the outer face of the tube T may have the stepped portion P as shown in the second embodiment to prevent damage of the tube T.

Referring to FIG. 8, unlike FIG. 2, etc., the number of the rows and columns of the induction magnets 100 is different, but this means that the number of the induction magnets 100 is variable according to the number and the size of the tube.

Referring to FIG. 8, the tube-fixing member 322a may be disposed as in the embodiment 1, but may be replaced by the tube-fixing member 322b as in the embodiment 2.

The elements that have reference numerals but not described here are same as in the first embodiment and/or second embodiment.

[Fourth Embodiment] Multi-Well Plate Type Magnetic Particle Separating Device

On the other hand, a multi-well plate type magnetic particle separating device will be explained referring to FIG. 9 through FIG. 11.

Referring to FIG. 9 through FIG. 11, like the first embodiment, induction magnets 100, induction magnet fixing parts 200 for fixing the induction magnets 100, a body 300, etc. are equipped. Additionally, a body position fixing part 400 is further equipped for the body 300 to be fixed to the induction magnet fixing part 200 therebetween. In the first embodiment, the induction magnet fixing part 200 is installed at the side of the body 300, but the body 300 is fixed to an upper portion of the induction magnet fixing part 200 in the second embodiment.

Referring to FIG. 10, the induction magnet fixing part 200 has induction magnet fixing holes 210 for fixing the induction magnets 100, respectively. The induction magnets 100 may be fixed to the induction magnet fixing holes 210 through a tight fit, a bond, etc.

Unlike FIG. 2, etc., it is preferable that the induction magnets 100 has a cylindrical shape with enough height.

In the present embodiment, 96 well plate is adopted, but not limited to this and various well plates may be adopted. In this case, the number of induction magnets may be adjusted according to the number of rows and columns of the multi-well pate. In case of 96 well plate, 8*12 number of entry holes (310; ninety six entry holes), and a compartment wall 320 is disposed therebetween. Referring to FIG. 11, 9*13 number of spaces (one hundred seventeen spaces) are formed, which is greater by one in the row and column in a lower portion of the entry hole 310. In order that the induction magnets 100 are disposed in those spaces one by one, it is preferable that one hundred seventeen induction magnets 100 are inserted into and fixed to the induction magnet fixing part 200.

In order to provide the above spaces, it is preferable that a lower portion of the entry hole 310 is smaller than an upper portion of the entry hole 310 in a cross-sectional area.

On the other hand, referring to FIG. 10, in order that the body 300 is fixed to the induction magnet fixing part 200, the body position fixing part 400 is disposed therebetween.

Referring to FIG. 10, the body position fixing part 400 may include a compressing member 410 and receiving portion 420 receiving the compressing member 410.

The compressing member 410 may be an o-ring made of rubber or silicone as described above, for preventing deformation or damage of the body 300 and separation of the body 300, when the body 300 is inserted.

The body position fixing part 400 may be combined to the induction magnet fixing part 200 through various methods, for example such as a screw connection, a bolt connection, a snap-in connection, a magnet connection, etc. The hole H is for the connection between the body position fixing part 400 and the induction magnet fixing part 200.

[Fifth Embodiment] Method of Separating Magnetic Particles Using the First Through Third Embodiment Hereinafter, a method of separating and purifying nucleic acid using the magnetic particle separating device of the first through third embodiments, will be explained.

Firstly, magnetic particles are mixed with gene material, and provided to the tube T in order to separate nucleic acid by using magnetic particles (S100).

Referring to FIG. 1 through FIG. 8, the tube T is inserted into at least one of entry holes 310 along a height direction of the body 300 (S200).

At this time, the tube-fixing member 322a, 322b compresses the outer surface of the tube T, so that the tube T is fixed to the body 300 (S200).

The induction magnet fixing part 200 to which the induction magnets 100 is fixed is fixed to a side of the body 300 (S300). The order of the above step S100 through S300 may be changed for convenience of a user.

The magnetic particle combined with the gene material is attracted toward the induction magnets 100 through magnetic fields generated by the induction magnets (100) (S400). Residue liquid except for the magnetic particle combined with the gene material is removed from the tube T (S500).

The induction magnet fixing part 200 fixed to the body 300 is separated from the body 300 to remove magnetic field applied to the body 300 (S600). In order to separate the magnetic particles and nucleic acid remaining in the tube T, cleaning solution is provided to the tube T (S700). As a result, the nucleic acid is effectively separated and purified.

The above step of providing the cleaning and separating solution (S700) may be performed several times.

[Sixth Embodiment] Method of Separating Magnetic Particles

Hereinafter, a method of separating and purifying nucleic acid using the magnetic particle separating device of the fourth embodiment, will be explained.

Firstly, magnetic particles are mixed with gene material, and provided to the multi-well plate in order to separate nucleic acid by using magnetic particles (S100).

Referring to FIG. 9 through FIG. 11, in order that the induction magnets 100 are inserted into between unit wells of the multi-well plate body 300, the multi-well plate body 300 is fixed to the body position fixing part 400 (S200~S300).

At this time, the compressing member 410 in the body position fixing part 400 compresses the outer surface of the multi-well plate body 300, so that the multi-well plate body 300 is fixed to the body position fixing part 400 (S200). The order of the above step S100 through S200 may be changed for convenience of a user.

The magnetic particle combined with the gene material is attracted toward the induction magnets 100 through magnetic fields generated by the induction magnets (100) (S400).

Residue liquid except for the magnetic particle combined with the gene material is removed from the multi-well plate body 300 (S500).

The body position fixing part 400 fixed to the multi-well plate body 300 is separated from the multi-well plate body 300 to remove magnetic field applied to the multi-well plate body 300 (S600).

In order to separate the magnetic particles and nucleic acid remaining in the unit well of the multi-well plate body 300, cleaning solution is provided to the unit well of the multi-well plate body 300 (S700).

As a result, the nucleic acid is effectively separated and purified.

The above step of providing the cleaning and separating solution (S700) may be performed several times.

[Experimental Embodiment] Method of Separating Plasmid DNA Using the Magnetic Particle Separating Device of the Present Invention Hereinafter, a method of separating plasmid DNA using the magnetic particle separating device of the present invention, will be explained. This is one example, and includes a method of separating nucleic acid, protein, etc. extensively.

In order to separate a target plasmid DNA, cell destruction solution is prepared. The cell destruction solution may be obtained through a chemical cell destruction method, and this includes a method used by a person skilled in the art.

Magnetic particles are provided to the prepared cell destruction solution so that cell protein denaturalized aggutinates, cell destruction particles and the magnetic particles are combined. Therefore, supernatant is obtained. In the method of obtaining the supernatant, the magnetic particle separating device of the present invention may be used.

8M guanidine-hydrogen chloride, 100% ethanol, and magnetic particles are provided to the obtained supernatant to mix them. Through the mixing process, the target plasmid DNA is combined with the magnetic particles.

In order to separate the plasmid DNA-magnetic particles combined with each other, magnetic fields are applied/ removed by using the magnetic particle separating device of the present invention so that the plasmid DNA-magnetic particles are attracted toward the induction magnet fixing part in the tube. Therefore, impurity solution except for the plasmid DNA-magnetic particles can be removed.

Cleaning solution is provided to the tube containing only the plasmid DNA-magnetic particles and not the impurity solution to perform cleaning process. In this process, a method applying/removing magnetic fields through the induction magnetic fixing part 200 is used.

Also, through applying/removing magnetic fields to/from the plasmid DNA-magnetic particles, the target protein can be separated from the plasmid DNA-magnetic particles.

Figure 12:
FIG. 12 is an electrophoresis picture showing a result of plasmid DNA separation performed by the magnetic particle separating device according to the present invention.

FIG. 12 is an electrophoresis picture showing a result of the plasmid DNA separated by the magnetic particle separating device according to the present invention. In comparison with a column type plasmid kit, similar effect can be verified.

INDUSTRIAL APPLICABILITY

According to the present invention, applying and removing magnetic fields are convenient. Therefore, it can be effectively used for extracting nucleic acid or protein.

Further, the tube can be easily inserted into and tightly fixed to the body so that residue material can be easily removed while the nucleic acid and the magnetic particles are attracted by magnetic material.

The invention claimed is:

1. A magnet particle separating device comprising:
a plurality of induction magnets with magnetic fields for attracting magnetic particles;
an induction magnet fixing part having induction magnet fixing holes into which the induction magnets are inserted for fixing the induction magnets; and
a body with which the induction magnet fixing part is combined, the body having entry holes, including first entry hole and a second entry hole adjacent to each other, each formed downward from a top surface of the body along a height direction which is a vertical direction for inserting a tube therein such that the entry holes correspond to array position of the induction magnets, and the body having a compartment wall comparting the first entry hole for receiving a first tube therein and the second entry hole for receiving a second tube therein,
wherein plural induction magnets of the plurality of induction magnets are arranged in the vertical direction along each entry hole,
wherein,
the compartment wall comprises: an insertion hole formed on the compartment wall along a longitudinal direction of the compartment wall, which is orthogonal to the height direction; and a single tube-fixing member positioned in the insertion hole, exposed to the first entry hole and the second entry hole, and configured to compress an outer surface of the first tube being inserted along the height direction into the first entry hole and an outer surface of the second tube being inserted along the height direction into the second entry hole to fix the first tube and the second tube to the body, or
the body comprises: a groove portion penetrating the compartment wall along a width direction of the compartment wall, which is orthogonal to the height direction and the longitudinal direction; and a single tube-fixing member positioned in the groove portion, arranged along the width direction, exposed to the first entry hole and the second entry hole, and configured to press an outer surface of the first tube being inserted along the height direction into the first entry hole and an outer surface of the second tube being inserted along the height direction into the second entry hole to fix the first tube and the second tube to the body.

2. The magnet particle separating device of claim 1, wherein a depth of the each entry hole is greater than a length of the tube to be inserted into an entry hole of the entry holes such that a bottom surface of the tube is spaced apart from a bottom surface of the entry hole by a distance when the tube is inserted into the entry hole.

3. The magnet particle separating device of claim 1, wherein an end portion of an induction magnet fixing hole of the induction magnet fixing holes protrudes for fixing an induction magnet of the plurality of induction magnets when the induction magnet is inserted into the induction magnet fixing hole.

4. The magnet particle separating device of claim 1, wherein the induction magnet fixing part has a first combination magnet fixing hole formed at edge portion of a surface on which the induction magnet fixing holes are formed, the first combination magnet fixing hole receiving a first combination magnet for a combination with the body, and
wherein the body has a second combination fixing hole formed at a position which faces the first combination magnet fixing hole of the induction magnetic fixing part when the body and the induction magnet fixing part are assembled, the second combination fixing hole receiving a second combination magnet for a combination with the induction magnet fixing part through a magnetic force.

5. The magnet particle separating device of claim 1, wherein a first end of an induction magnet of the plurality of induction magnets is fixed to an induction magnet fixing hole of the induction magnet fixing holes of the induction magnet fixing part, and a second end of the induction magnet opposite to the first end protrudes upward, and the each entry hole has an upper portion and a lower portion smaller than the upper portion in a cross-sectional area, for providing a lower portion of the body with a space for the induction magnet of the plurality of induction magnets to be disposed between the compartment wall and an adjacent compartment wall.

6. The magnet particle separating device of claim 5, further comprising a body position fixing part disposed between the body and the induction magnet fixing part, the body position fixing part comprising:
a compressing member for compressing an outer surface of the body for the body to be fixed to the induction magnet fixing part to which the plurality of induction magnets are fixed; and
a receiving portion receiving and fixing the compression member.

7. A method of separating and purifying nucleic acid or protein using the magnet particle separating device of claim 1, the method comprising:
mixing magnetic particles with gene material to provide a mixture to the tube in order to separate nucleic acid by using magnetic particles;
fixing the tube to the body;
combining the induction magnet fixing part with the plurality of induction magnets fixed thereto with the body;
attracting magnetic particles combined with the gene material toward the plurality of induction magnets through magnetic fields generated by the plurality of induction magnets;
removing residue solution except for the magnetic particles combined with the gene material from the from the tube; and
separating the induction magnet fixing part from the body to remove magnetic fields applied to the body.

8. The method of claim 7, further comprising:
providing cleaning solution or separation solution to the tube to separate the nucleic acid or protein from the magnetic particles in the tube after removing magnetic fields.

* * * * *